(12) United States Patent
Buchanan

(10) Patent No.: US 10,357,643 B2
(45) Date of Patent: Jul. 23, 2019

(54) SYSTEM FOR ENHANCED SEALING OF COUPLED MEDICAL FLUID LINES AND METHOD

(71) Applicant: Sheila Buchanan, West Nyack, NY (US)

(72) Inventor: Sheila Buchanan, West Nyack, NY (US)

(73) Assignee: BLUE I.V. LLC, West Nyack, NY (US)

( * ) Notice: Subject to any disclaimer, the term of this patent is extended or adjusted under 35 U.S.C. 154(b) by 150 days.

(21) Appl. No.: 15/673,027

(22) Filed: Aug. 9, 2017

(65) Prior Publication Data
US 2018/0221641 A1    Aug. 9, 2018

Related U.S. Application Data

(60) Provisional application No. 62/455,359, filed on Feb. 6, 2017.

(51) Int. Cl.
*A61M 39/10*    (2006.01)
*A61M 39/20*    (2006.01)

(52) U.S. Cl.
CPC ...... *A61M 39/105* (2013.01); *A61M 39/1011* (2013.01); *A61M 39/20* (2013.01); *A61M 2039/1027* (2013.01); *A61M 2039/1088* (2013.01)

(58) Field of Classification Search
CPC .. A61M 39/10; A61M 39/1011; A61M 39/20; A61M 2039/1033; A61M 2039/1038; A61M 2039/1088
See application file for complete search history.

(56) References Cited

U.S. PATENT DOCUMENTS

| | | | |
|---|---|---|---|
| 4,076,023 A | 2/1978 | Martinez | |
| 4,993,133 A | 2/1991 | Goeserich | |
| 5,047,021 A | 9/1991 | Utterberg | |
| 5,230,706 A | 7/1993 | Duquette | |
| 5,536,258 A * | 7/1996 | Folden | A61M 39/16 285/331 |
| 5,700,248 A | 12/1997 | Lopez | |
| 7,004,934 B2 * | 2/2006 | Vaillancourt | A61M 39/14 604/164.01 |
| 8,083,237 B2 | 12/2011 | Smith | |
| 2014/0100533 A1 | 4/2014 | Lyons | |
| 2014/0167411 A1 | 6/2014 | Kimbrell | |

* cited by examiner

*Primary Examiner* — Laura A Bouchelle
(74) *Attorney, Agent, or Firm* — Medley, Behrens & Lewis LLC

(57) ABSTRACT

A system for enhanced sealing of coupled medical fluid or vascular access lines includes a male fitting, a female fitting, and an annular collar seal which is affixable to the male fitting. After the annular collar seal is affixed to the male fitting, the female fitting is placed through the collar and connected to the male fitting.

20 Claims, 5 Drawing Sheets

SYSTEM FOR ENHANCED SEALING OF COUPLED MEDICAL FLUID LINES AND METHOD

CROSS-REFERENCE TO RELATED APPLICATION(S)

The present application is related to and claims priority to U.S. Provisional Patent Application No. 62/455,359 filed Feb. 6, 2017, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of closure caps, seals or plugs for connectors or open ends of tubes of existing art and more specifically relates to medical fluid and vascular access line couplings.

RELATED ART

Many patients need intravenous lines inserted when visiting the emergency room or have been admitted into the hospital for treatment. Others may need intravenous treatment on an outpatient basis. In either case, often patients are required to keep an intravenous line in place over a period of days. In an outpatient situation, patients need to maintain their personal hygiene by showering, bathing and the like, resulting in the intravenous line and connector being exposed to various contaminating fluids from these activities. When a patient is in an emergency room or hospital setting, intravenous lines may remain in place for extended periods due to varying perspectives on the frequency at which they should be changed. Within the medical community, there is currently lack of agreement as to when an intravenous line and needleless connectors should ideally be replaced to avoid contamination to a patient. It is very important to patient health that the intravenous line remain sanitary to remove or minimize the risk of a secondary infection. Central line associated blood stream infections (CLABSI) are caused by contaminants such as air, liquid, micro-organisms and other biological materials entering the system. After contaminants have entered the system, patients are at significant risk for infection, sepsis, organ failure, and death. Hospitals incur increased costs and are required to report such incidents. An effective method of prevention of these types of infections is needed.

U.S. Pat. No. 5,230,706 to Duquette relates to a bi-directional valve assembly used in needleless injection or infusion ports. The described bi-directional valve assembly used in needleless injection or infusion ports includes a bi-directional valve assembly disposed within an infusion system to permit the administration of an infusion solution without the use of a needle. The bi-directional valve assembly is a two-way spring valve which comprises: a spring means, a valve port, and a valve plunger having a sealing means and a conduit means disposed thereabout, wherein the spring means is connected to the valve plunger in such a way as to permit the opening of the conduit means when the spring means is recoiled such that the sealing means is not in contact with the valve port and to permit the closing of the conduit means when the spring means is expanded such that the sealing means is in contact with the valve port; whereby the bi-directional valve assembly is capable of opening and closing the infusion system.

SUMMARY OF THE INVENTION

In view of the foregoing disadvantages inherent in the art of medical fluid and vascular access line couplings, the present disclosure provides a novel system for enhanced sealing of coupled medical fluid and vascular access lines and method. The general purpose of the present disclosure, which will be described subsequently in greater detail, is to provide an improved system to seal-coupled medical fluid and vascular access lines at exposed connection sites such as male Luer lock connections, and method of use thereof. The improved system may maintain a sterile system over time, and thereby reduce rates of infection in patients requiring extended use of intravenous lines as part of treatment.

A system for enhanced sealing of coupled medical fluid and vascular access lines and method is disclosed herein. The system for enhanced sealing of coupled medical fluid lines includes a male fitting, a female fitting, and an annular collar seal. The male fitting is made of rigid medical grade polymers, and includes a male connector, a locking collar, and a female lock element fixed to the locking collar, the female lock element circumscribing the male connector, the locking collar circumscribing the female lock element, the male connector fluidly coupled to a first fluid line or needleless connector. The female fitting is made of rigid medical grade polymers, and includes a female connector, a connector guide extending radially and axially from the female connector, and a male lock element fixed to the connector guide axially opposite the female connector and extending radially outward from the connector guide, the female connector fluidly coupled to a second fluid line or needleless connector and configured to sealingly mate with the male connector, the male lock element configured to removably couple with the female lock element. The annular collar seal is made of a non-rigid, medical grade polymer and is affixable to the male fitting, the annular collar seal having an outer sealing lip and an inner sealing lip, the outer sealing lip configured to circumscribe and seal against the locking collar of male fitting, the inner sealing lip configured to deformably permit passage of the male lock element of the female fitting through the inner sealing lip and into the locking collar, and further configured to seal against the connector guide after said passage of the male lock element.

According to another embodiment, a method of using the system for enhanced sealing of coupled medical fluid and vascular access lines is also disclosed herein. The method of using the system for enhanced sealing of coupled medical fluid lines includes a first step of providing a system for enhanced sealing of coupled medical fluid and vascular access lines having a threaded connection, the system including a male Luer lock fitting, a female Luer lock fitting, and an annular collar seal, the male Luer lock fitting including a male connector, a locking collar, and a female lock element fixed to the locking collar, the female Luer lock fitting including a female connector, a connector guide extending radially and axially from the female connector, and a male lock element fixed to the connector guide axially opposite the female connector and extending radially outward from the connector guide, and the annular collar seal affixable to locking collar of the male Luer lock fitting and configured to permit passage of the connector guide and the male lock element of the female Luer lock fitting into the locking collar of the male Luer lock fitting, and further configured to seal against the connector guide after said passage of the connector guide and the male lock element. The method further includes additional steps of affixing the annular collar seal to the male Luer lock fitting such that the annular collar seal seals against the locking collar; fluidly coupling a first medical fluid line to the male connector of the male Luer lock fitting and a second medical fluid line to the female connector of the female Luer lock fitting; inserting the connector guide and the male lock element of the female Luer lock fitting through the annular collar seal and onto the male Luer lock fitting; coupling the male lock element of the female Luer lock fitting with the female lock element of the male Luer lock fitting; and transferring a fluid between the first medical fluid line and the second medical fluid line via the male connector of the male Luer lock fitting and the female connector of the female Luer lock fitting.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a system for enhanced sealing of coupled medical fluid and vascular access lines and method, constructed and operative according to the teachings of the present disclosure.

The various embodiments of the present invention will hereinafter be described in conjunction with the appended drawings, wherein like designations denote like elements.

DETAILED DESCRIPTION

Figure 1:
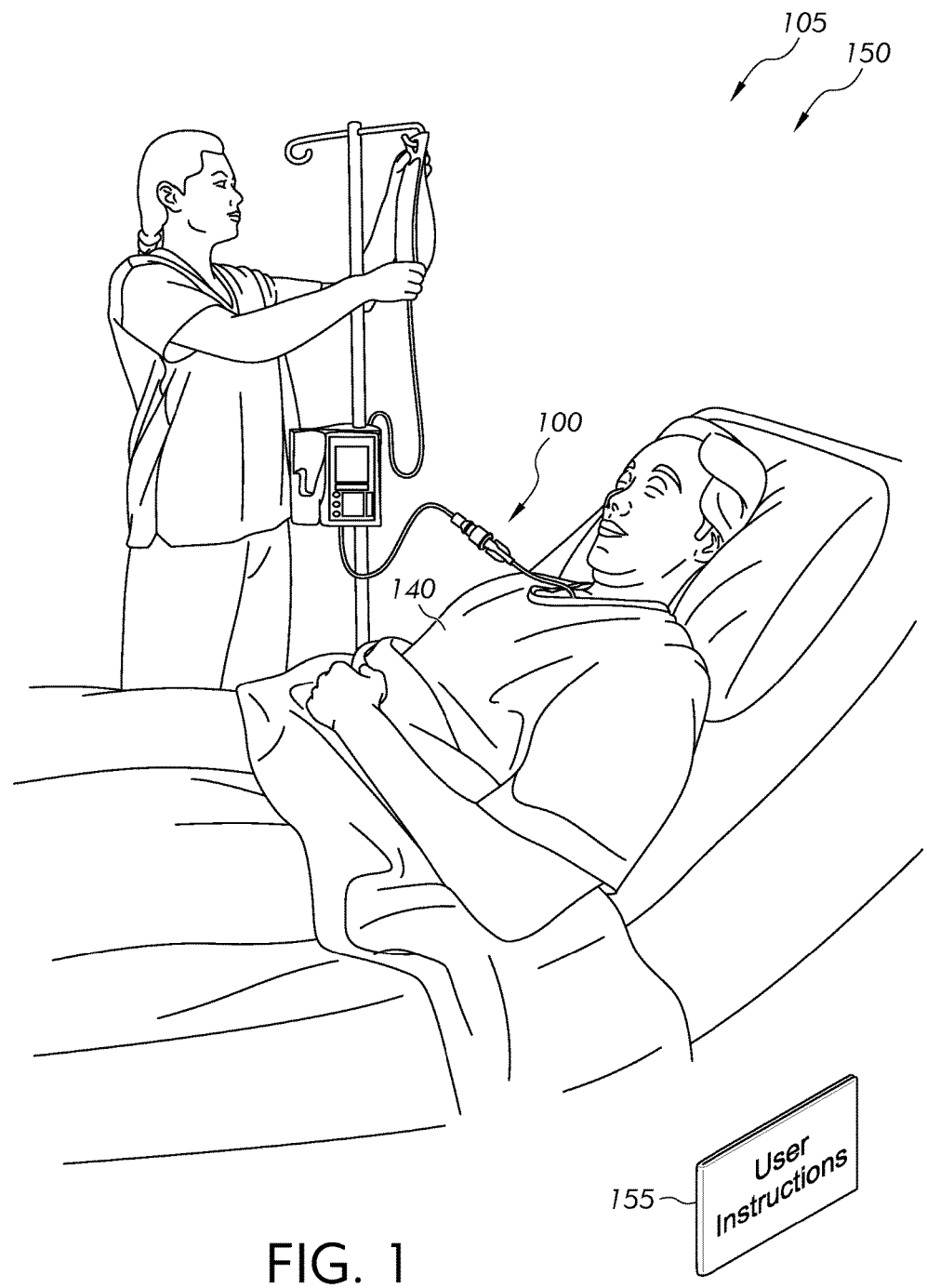
FIG. 1 is a perspective view of the system for enhanced sealing of coupled medical fluid lines during an 'in-use' condition, according to an embodiment of the disclosure.

As discussed above, embodiments of the present disclosure relate to medical fluid and vascular access line couplings, and more particularly to a system for enhanced sealing of coupled medical fluid and vascular access lines and method, as used to improve sealing of coupled medical fluid and vascular access lines to maintain a sterile connection. A sterile connection is critical in preventing Central Line Associated Blood Stream Infections (CLABSI) and other blood stream infections in patients requiring intravenous connections or use of any vascular access devices for extended periods. Vascular access devices are generally defined as tubing inserted into peripheral or central vessels, used primarily to administer fluids and medications, monitor pressures, and collect blood. Likewise, central lines are generally defined as intravenous lines that are inserted into large veins typically located in the neck or near the heart for therapeutic or diagnostic purposes, for example to administer medicines or fluids, or to withdraw blood. These lines inserted into larger vessels are particularly helpful in achieving faster rates of infusion of fluids or medication in emergency or intensive care settings.

Generally, the present disclosure provides for an improved seal for central lines and other intravenous connections to prevent air, liquid, micro-organisms, and other contaminants from entering the blood stream. It creates an air tight, liquid proof seal around any threaded medical device compatible with Luer locks, requiring a sterile connection. The seal will assist in reducing infections, and therefore hospital admission days, CLABSIs, other reportable incidents, and most importantly mortality rates will decrease. It prevents everyday contaminants, such as shower water, emesis, urine, and stool from entering the bloodstream at exposed connection points. The present disclosure provides for improved sealing to maintain a sterile connection in central line and other medical devices connected to the blood stream in any location where male Luer lock fittings are used.

The present disclosure may be used with male Luer lock fittings to connect a wide variety of vascular access devices to a hub. The hub typically has a female end having a threaded or lug style locking element which is compatible to connect with the threaded collar of a male Luer lock extending from any vascular access device connected to a patient. Hubs may connect to dialysis catheters, central lines, intravenous lines, and any device which accesses a patient's venous system. If no intravenous fluid is required, the end of the catheter or central line hub may be capped off with a needleless connector utilizing the present disclosure. If an intravenous line is connected to a patient and no intravenous therapy is desired at the present time, the male Luer lock located at the end of the intravenous line may be sealed and a cap may be used with the present disclosure until further therapy is required. In other instances, the present disclosure may be used in conjunction with a needleless connector with a female end having a threaded or lug style locking element which is compatible to connect with the threaded collar of a male Luer lock.

The present disclosure may be fabricated for compatibility with current standards and requirements set forth by the International Standards Organization. ISO 594 is currently in use, however ISO 80369-7 will supersede ISO 594 for medical equipment. The standard consists of eight separate tests as follows: 1 Gauging: A dimensional check is performed using a calibrated plug gauge; 2 Liquid Leakage: Ensures that the sample Luer does not leak when pressurized with water; 3 Air Leakage: Ensures that the sample Luer does not leak when a vacuum pressure is applied; 4 Separation Force: Ensures that the sample Luer remains attached to the reference fitting when an axial load is applied; 5 Ease of Assembly: Ensures that the sample Luer can be assembled with minimum axial force and torque; 6 Unscrewing Torque: Ensures that the sample Luer remains attached under a specific unscrewing (counter-clockwise) torque; 7 Resistance to Overriding: Ensures that the threads cannot be overridden by a specific screwing (clockwise) torque; 8 Stress Cracking: Ensures that the sample Luer does not crack when assembled for 48 hours.

A color coding system may be used with the present disclosure in conjunction with colored intravenous lines for example, to identify various intravenous administrations for a given patient. More specifically, the annular collar seal may be color matched to tinted intravenous lines or other connectors to further assist with distinguishing between differing medications supplied to a patient, as one example.

Biocompatibility requirements for medical components are becoming increasingly stringent in order to prevent patient rejection, infection, and adverse effects such as allergic reactions. Vascular access devices (VADs) are one category of medical components which includes various types of devices which are inserted into veins via peripheral or central blood vessels for diagnostic or therapeutic reasons, such as blood sampling, administration of medication or fluids, and blood transfusions. To avoid the above mentioned concerns with vascular access devices, they are overwhelmingly fabricated from medical grade polymers. Medical grade as used herein is defined as a material, in this instance a polymeric material, which has been tested for biocompatibility and deemed appropriate to be used for medical applications. Medical grade polymers are specifically designed to be used in, on or in contact with the body. All raw materials, intermediate products, and finished products for medical grade use are manufactured with appropriate regulatory standards and in high enough purity such it can be used for medical purposes safely in patients.

In addition to use of medical grade polymers, all medical devices used in intravenous therapy require thorough sterilization. Sterilization involves using chemicals, temperature, gas and/or pressure to kill or inactivate all disease-causing bacteria, spores, fungi and viruses. The United States Food and Drug Administration (FDA) recognizes three categories of sterilization methods currently used to sterilize medical devices in manufacturing settings: Traditional, Non-traditional, and Novel Non-traditional. Examples of each are illustrated in Table 1 below.

TABLE 1

Examples of Sterilization Methods for Medical Devices in Manufacturing Settings

| TRADITIONAL | NON-TRADITIONAL | NOVEL NON-TRADITIONAL |
|---|---|---|
| Dry Heat | Hydrogen Peroxide ($H_2O_2$)/ Gas Plasma | Chlorine Dioxide ($ClO_2$) |
| Moist Heat | Ozone ($O_3$) | Ethylene Oxide - ETO-in-a-bag (Diffusion method, Injection method) |
| ETO (fixed chamber) | | Pulsed Light |
| Radiation (gamma, E-beam) | | Microwave Radiation |
| | | Sound Waves |
| | | Vaporized Chemical Sterilant Systems (e.g. hydrogen peroxide, peracetic acid) |

Some traditional sterilization methods have been found to be unsuitable for medical products as these products cannot support high temperature sterilization processes. An alternative, often used process for sterilization utilizes Ethylene Oxide (EtO) gas with elevated temperature and humidity. This has become the preferred method for many medical products due to its relatively low processing temperatures of nominally 118 degrees Fahrenheit and relative humidity of approximately 65%. Materials selected for the system for enhanced sealing of coupled medical fluid lines, including those for the annular collar seal of the system should be done so with emphasis on corrugate strength and chemical stability over time to ensure compatibility with the sterilization procedures of Table 1, as well as any future processes developed for sterilization of medical products.

Referring now more specifically to the drawings by numerals of reference, there is shown in FIGS. 1-5, various views of a system for enhanced sealing of coupled medical fluid lines, 100.

FIG. 1 shows a system for enhanced sealing of coupled medical fluid and vascular access lines during an 'in-use' condition 150, according to an embodiment of the present disclosure. Here, the system for enhanced sealing of coupled medical fluid and vascular access lines (system 100) may be beneficial for use by a user 140 to maintain a more sealed connection over prolonged use of intravenous and vascular access lines in a patient. Ideally, this may potentially lead or aid in decreasing or mitigating central line and other blood stream related infection rates, as well as decreasing associated mortality rates.

According to one embodiment, the system for enhanced sealing of coupled medical fluid and vascular access lines lines 100 may be arranged as a kit 105. In particular, the system 100 may further include a set of instructions 155. The instructions 155 may detail functional relationships in relation to the structure of the system 100 such that the system for enhanced sealing of coupled medical fluid and vascular access lines 100 can be used, maintained, or the like, in a preferred manner.

Figure 2A:
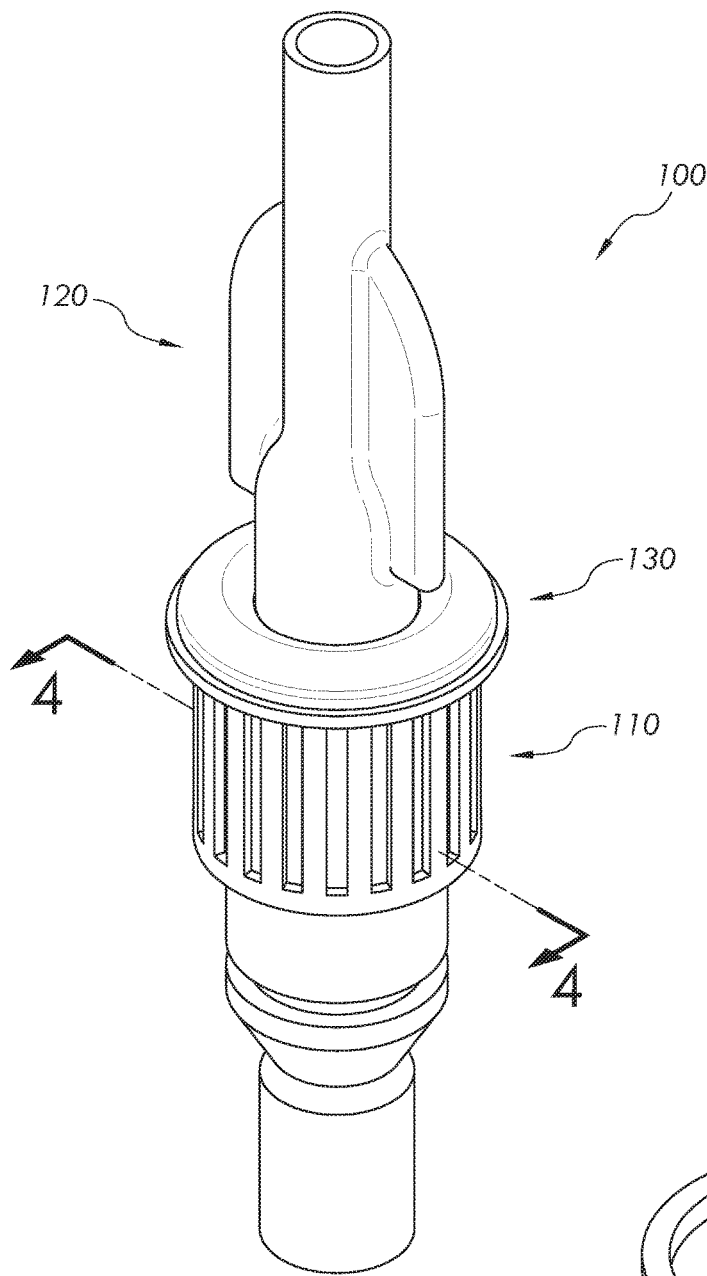
FIG. 2A is a perspective view of the system for enhanced sealing of coupled medical fluid and vascular access lines of FIG. 1, illustrating the male and female fittings, and the annular collar seal, according to an embodiment of the present disclosure.

FIG. 2A is a perspective view of the system for enhanced sealing of coupled medical fluid and vascular access lines of FIG. 1, illustrating the male and female fittings, and the annular collar seal, according to an embodiment of the present disclosure. As illustrated, the system 100 may include a male fitting 110, a female fitting 120, and an annular collar seal 130. The male fitting 110 may be made of rigid medical grade polymers. The female fitting 120 may be similarly made of rigid medical grade polymers. Also, the annular collar seal 130 may be made of non-rigid medical grade polymers.

The annular collar seal 130 may further be affixable to the male fitting 110. In particular, the annular collar seal 130 may be configured to further seal or otherwise provide a barrier around any male Luer lock connection, for example, that is part of a vascular access device. Beneficially, the annular collar seal 130 may aid in preventing entry of contaminants such as shower water, emesis, urine, and stool into a patients fluid delivery system during extended use. As such, the system 100 may aid in or be useful to maintain sterility of vascular access devices over time, and thereby reduce rates of infection as well as mortality rates in those patients requiring extended use of intravenous lines as part of treatment.

Figure 2B:
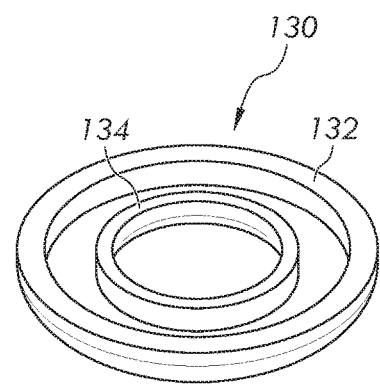
FIG. 2B is a detail view of the annular collar seal of the system for enhanced sealing of coupled medical fluid lines of FIG. 1, according to an embodiment of the present disclosure.

FIG. 2B is a perspective view of the annular collar seal 130 of FIG. 2A in isolation and from an interface perspective to illustrate the interior of the seal. As shown, the annular collar seal 130 may have an outer sealing lip 132 and an inner sealing lip 134, the outer sealing lip may be configured to circumscribe and seal against an outer perimeter of male fitting 110 (FIG. 2A), such as a locking collar 116 (FIG. 3A) of the male fitting 110. The inner sealing lip 134 may be configured to deformably permit passage of a male lock element 126 (FIG. 3A) of the female fitting 120 through the inner sealing lip 134 and into the locking collar 116, and further configured to seal against a connector guide 122 (FIG. 3A) after said passage of the male lock element 126.

Figure 3A:
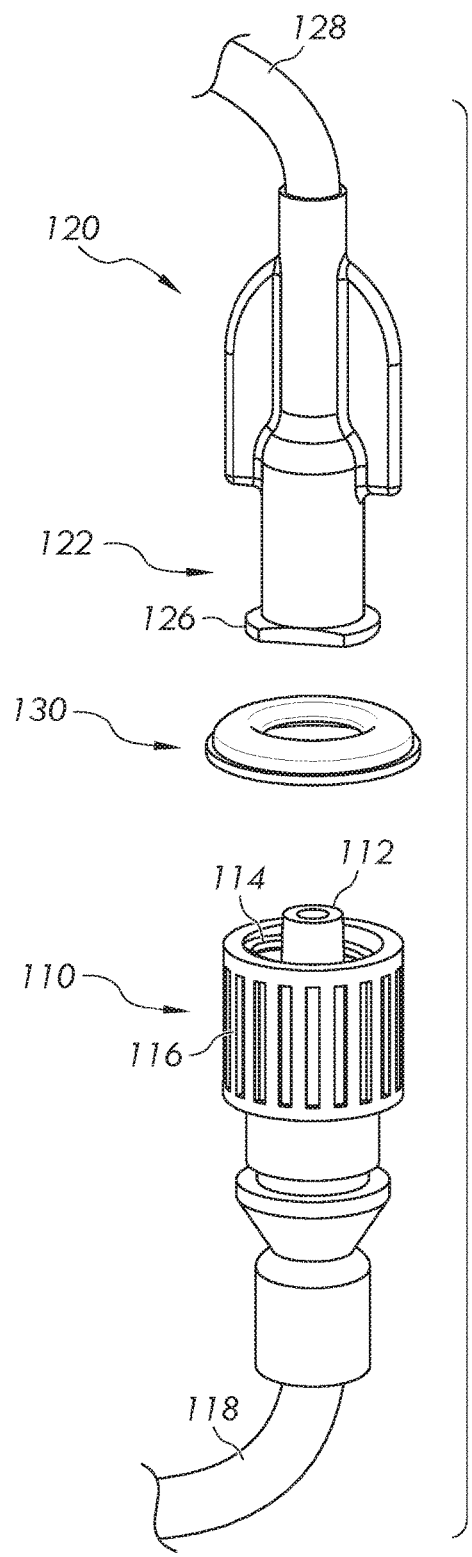
FIG. 3A is an assembly drawing of the system for enhanced sealing of coupled medical fluid lines of FIG. 1, illustrating a lug style lock element, according to an embodiment of the present disclosure.

FIG. 3A is an assembly view of the system 100 for enhanced sealing of coupled medical fluid and vascular access lines of FIG. 2, according to an embodiment of the present disclosure. As above, the system 100 may include the male fitting 110, the female fitting 120, and the annular collar seal 130. Here, the female fitting 120 is of a first exemplary type (lug).

The male fitting 110 may include a male connector 112, a locking collar 116 and a female lock element 114 fixed to the locking collar 116, the female lock element circumscribing the male connector 112, for example, on an interior surface of the locking collar 116. When assembled, the male connector 112 may be fluidly coupleable to a first fluid line 118.

The female fitting 120 may include a female connector 124, a connector guide 122 extending radially and axially from the female connector, and a male lock element 126 fixed to the connector guide axially opposite the female connector 124 and extending radially outward from the connector guide 122, the female connector fluidly coupled to a second fluid line 128 and configured to sealingly mate with the male connector 112, the male lock element 126 configured to removably couple with the female lock element 114. According to one embodiment, the male lock element 126 may be configured as a lug coupling such that it may removably coupled with the female lock element 114 via insertion and 90 degree locking rotation, or another toolless locking technique.

Figure 3B:
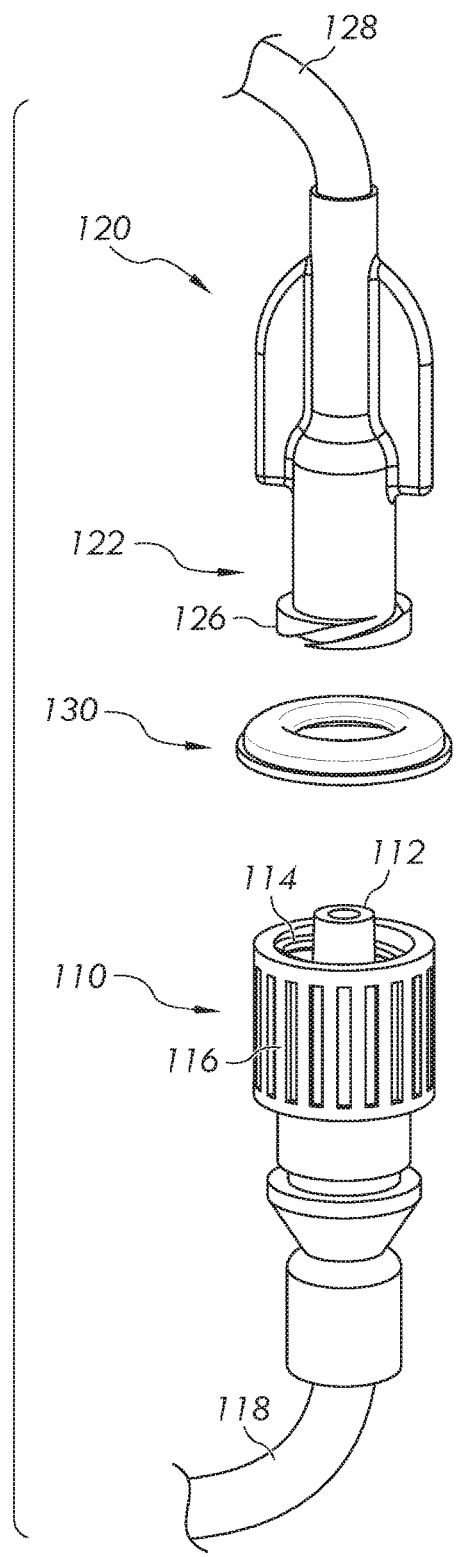
FIG. 3B is an assembly drawing of the system for enhanced sealing of coupled medical fluid and vascular access lines, illustrating a screw style lock element, according to another embodiment of the present disclosure.

FIG. 3B is an assembly view of the system 100 for enhanced sealing of coupled medical fluid lines, according to another embodiment of the present disclosure. As above, the system 100 may include the male fitting 110, the female fitting 120, and the annular collar seal 130. Here, the female fitting 120 is of a second exemplary type (screw). In particular, as shown, the male lock element 126 may be configured as a screw coupling such that it may removably coupled with the female lock element 114 via screw motion.

Figure 4:
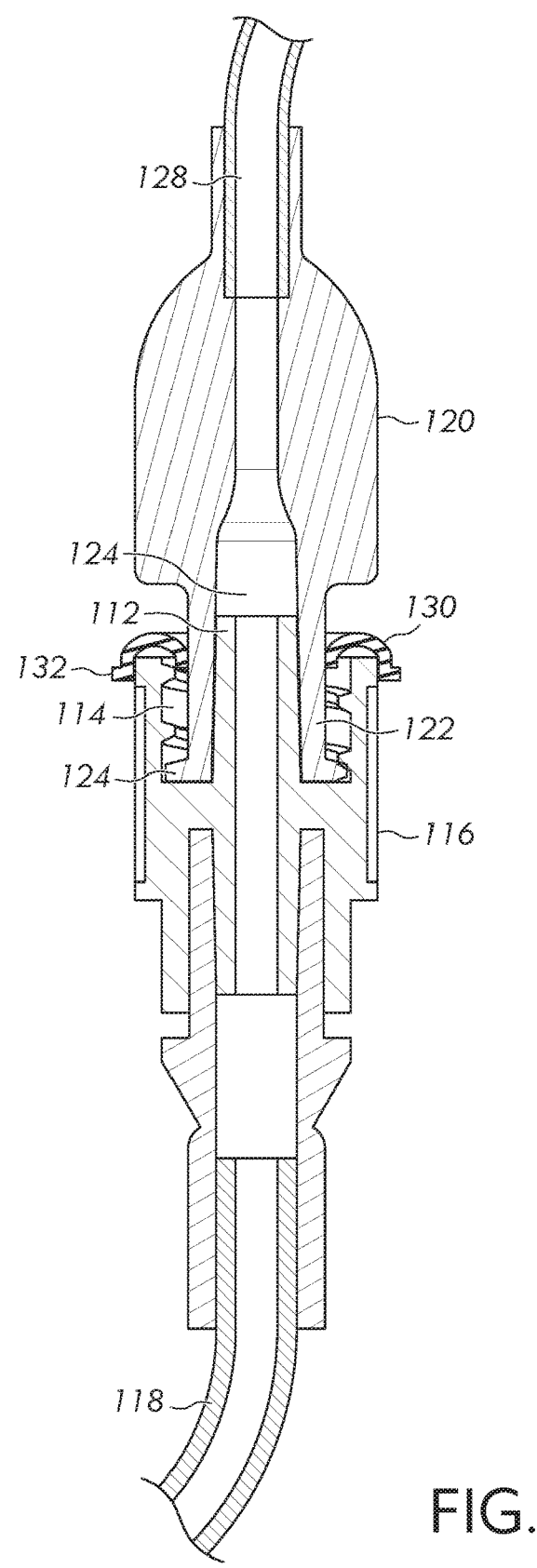
FIG. 4 is a cutaway view of the system for enhanced sealing of coupled medical fluid and vascular access lines of FIG. 1, according to an embodiment of the present disclosure.

FIG. 4 is a section view of the system 100 for enhanced sealing of coupled medical fluid lines of FIG. 2, according to an embodiment of the present disclosure. As depicted, the fluidly coupled connection between the first fluid line 118, the male connector 112, the female connector 124 and the second fluid line 128 may be appreciated.

The outer sealing lip 132 of the annular collar seal 130 is shown circumscribing and sealing the locking collar 116 of the male fitting 110 and also sealing a perimeter of the connector guide 122 of the female fitting 120, and may be configured to provide enhanced sealing of the male Luer lock connection.

Figure 5:
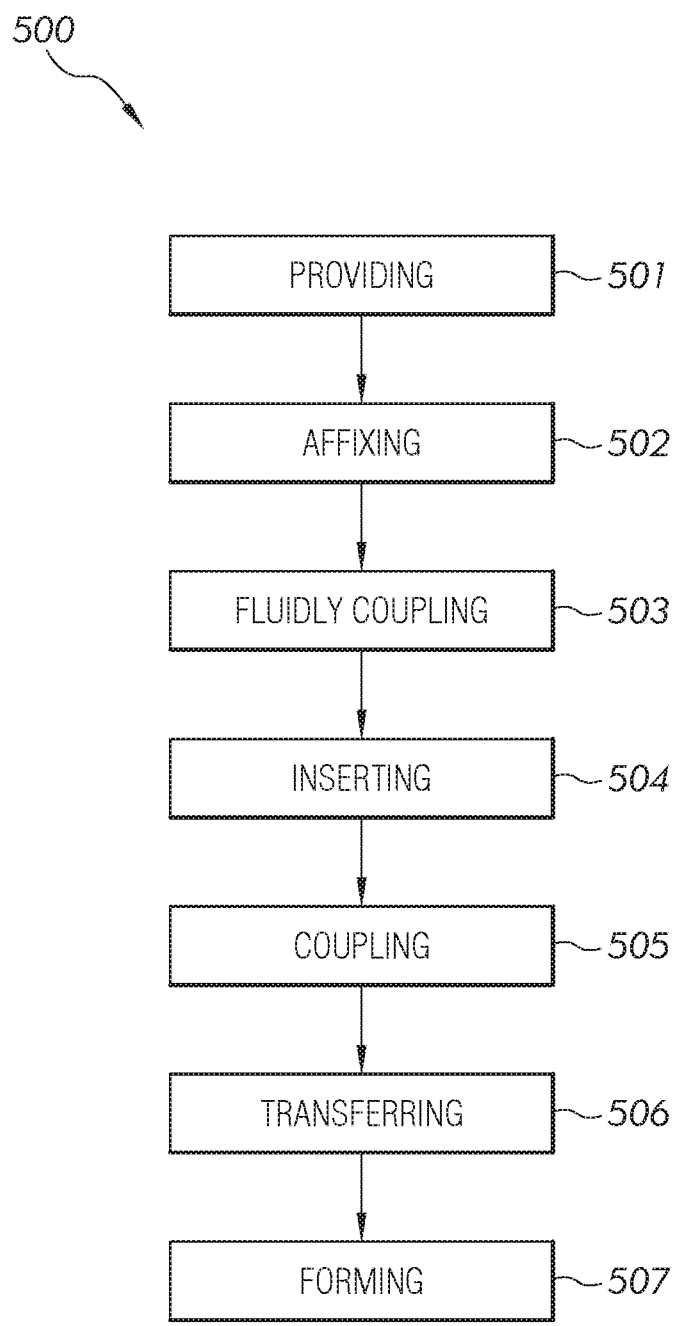
FIG. 5 is a flow diagram illustrating a method for enhanced sealing of coupled medical fluid and vascular access lines having a threaded connection, according to an embodiment of the present disclosure.

FIG. 5 is a flow diagram illustrating a method for enhanced sealing of coupled medical fluid and vascular access line according to an embodiment of the present disclosure. In particular, the method for enhanced sealing of coupled medical fluid and vascular access lines 500 may include one or more components or features of the system for enhanced sealing of coupled medical fluid and vascular access lines 100 as described above. As illustrated, the method for using the system for enhanced sealing of coupled medical fluid and vascular access lines 500 may include the steps of: step one 501, providing a system for enhanced sealing of coupled medical fluid and vascular access lines, the system including a male Luer lock fitting 110, a female Luer lock fitting 120, and an annular collar seal 130, the male Luer lock fitting 110 including a male connector 112, a locking collar 116, and a female lock element 114 fixed to the locking collar, the female Luer lock fitting 120 including a female connector 124, a connector guide 122 extending radially and axially from the female connector, and a male lock element 126 fixed to the connector guide 122 axially opposite the female connector and extending radially outward from the connector guide, and the annular collar seal 130 affixable to locking collar 116 of the male fitting 110 and configured to permit passage of the connector guide 122 and the male lock element 126 of the female Luer lock fitting 120 into the locking collar 116 of the male Luer lock fitting 110, and further configured to seal against the connector guide 122 after said passage of the connector guide and the male lock element 126; step two 502, affixing the annular collar seal 130 to the male Luer lock fitting such that the annular collar seal seals against the locking collar 116; step three 503, fluidly coupling a first medical fluid line 128 to the male connector 112 of the male Luer lock fitting 110 and a second medical fluid line 118 to the female connector 124 of the female Luer lock fitting; step four 504, inserting the connector guide 122 and the male lock element 126 of the female Luer lock fitting 120 through the annular collar seal 130 and onto the male Luer lock fitting 110; step five 505, coupling the male lock element 126 of the female Luer lock fitting 120 with the female lock element 114 of the male Luer lock fitting 110; and step six 506, transferring a fluid between the first medical fluid line 128 and the second medical fluid line 116 via the male connector 112 of the male Luer lock fitting 110 and the female connector 124 of the female Luer lock fitting 120. According to one embodiment, the method 500 may further include an additional step seven 507, forming a persistent seal between the annular collar seal and the male Luer lock fitting via at least one of a polymer weld or an adhesive bond.

It should be noted that step seven 507 is an optional step, and may not be implemented in all cases. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using the system for enhanced sealing of coupled medical fluid lines are taught herein.

The embodiments of the disclosure described herein are exemplary and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

Those with ordinary skill in the art will now appreciate that upon reading this specification and by their understanding the art of closure caps, seals or plugs for connectors or open ends of tubes as described herein, methods of closure caps, seals or plugs for connectors or open ends of tubes will be understood by those knowledgeable in such art.

What is claimed is new and desired to be protected by Letters Patent is set forth in the appended claims:

1. A system for enhanced sealing of coupled medical fluid and vascular access lines having a threaded connection, the system comprising:
   a male fitting made of rigid medical grade polymers, and including a male connector, a locking collar, and a female lock element fixed to the locking collar, the female lock element circumscribing the male connector, the locking collar circumscribing the female lock element, the male connector fluidly coupled to a first fluid line; and
   a female fitting made of rigid medical grade polymers, and including a female connector, a connector guide extending radially and axially from the female connector, and a male lock element fixed to the connector guide axially opposite the female connector and extending radially outward from the connector guide, the female connector fluidly coupled to a second fluid line and configured to sealingly mate with the male connector, the male lock element configured to removably couple with the female lock element; and
   an annular collar seal made of a non-rigid, medical grade polymer and affixable to the male fitting, the annular collar seal having an outer sealing lip and an inner sealing lip, the outer sealing lip configured to circumscribe and seal against the locking collar of the male fitting, the inner sealing lip configured to deformably permit passage of the male lock element of the female fitting through the inner sealing lip and into the locking collar, and further configured to seal against the connector guide after said passage of the male lock element.

2. The system of claim 1, wherein the male fitting is a male end of a Luer lock.

3. The system of claim 1, wherein the female fitting is a female end of a Luer lock.

4. The system of claim 1, wherein the locking collar and the female lock element of the male fitting are integrated together.

5. The system of claim 1, wherein the female lock element and the male lock element are configured as a screw coupling.

6. The system of claim 1, wherein the female lock element and the male lock element are configured as a lug coupling.

7. The system of claim 1, wherein one of the female fitting and the male fitting is configured as a hub of a vascular access device.

8. The system of claim 1, wherein the non-rigid medical grade polymer includes at least one of a thermoplastic elastomer, a silicone, or a styrene block copolymer.

9. The system of claim 1, wherein the inner sealing lip is configured to exert a compressive force on the connector guide and create a compressive seal against the connector guide.

10. The system of claim 1, wherein the annular collar seal is made of a sterilizable material.

11. The system of claim 1, wherein the locking collar of the male fitting is rotatable about the male connector.

12. The system of claim 1, wherein the annular collar seal has a cross sectional curvature along a radial of the annular collar seal between the inner sealing lip and the outer sealing lip, the cross sectional curvature extending away from the male fitting relative to a center axis of the annular collar seal and when affixed to the male fitting.

13. The system of claim 1, wherein the inner sealing lip is configured to provide a radial compressive seal against the connector guide when the female lock element is coupled to the male lock element.

14. The system of claim 1, wherein the outer sealing lip is sealed to the locking collar via a polymer weld.

15. The system of claim 1, wherein the outer sealing lip is sealed to the locking collar via an adhesive bond.

16. The system of claim 1, wherein the outer sealing lip is sealed to the locking collar via a compressive spring force seal.

17. A system for enhanced sealing of coupled medical fluid lines having a threaded connection, the system comprising:
   a male fitting made of rigid medical grade polymers, and including a male connector, a locking collar, and a female lock element fixed to the locking collar, the female lock element circumscribing the male connector, the locking collar circumscribing the female lock element, the male connector fluidly coupled to a first fluid line; and
   a female fitting made of rigid medical grade polymers, and including a female connector, a connector guide extending radially and axially from the female connector, and a male lock element fixed to the connector guide axially opposite the female connector and extending radially outward from the connector guide, the female connector fluidly coupled to a second fluid line and configured to sealingly mate with the male connector, the male lock element configured to removably couple with the female lock element; and
   an annular collar seal made of a non-rigid, medical grade polymer and affixable to the male fitting, the annular collar seal having an outer sealing lip and an inner sealing lip, the outer sealing lip configured to circumscribe and seal against the locking collar of male fitting, the inner sealing lip configured to deformably permit passage of the male lock element of the female fitting through the inner sealing lip and into the locking collar, and further configured to seal against the connector guide after said passage of the male lock element; and wherein the male fitting is a male end of a Luer lock;

wherein the female fitting is a female end of a Luer lock;

wherein the locking collar and the female lock element of the male fitting are integrated together;

wherein the female lock element and the male lock element are configured as a screw coupling;

wherein one of the female fitting and the male fitting is configured as a hub of a vascular access device;

wherein the non-rigid medical grade polymer includes at least one of a thermoplastic elastomer, a silicone, or a styrene block copolymer;

wherein the inner sealing lip is configured to exert a compressive force on the connector guide and create a compressive seal against the connector guide;

wherein the annular collar seal is made of a sterilizable material;

wherein the locking collar of the male fitting is rotatable about the male connector;

wherein the annular collar seal has a cross sectional curvature along a radial of the annular collar seal between the inner sealing lip and the outer sealing lip, the cross sectional curvature extending away from the male fitting relative to a center axis of the annular collar seal and when affixed to the male fitting;

wherein the inner sealing lip is configured to provide a radial compressive seal against the connector guide when the female lock element is coupled to the male lock element; and wherein the outer sealing lip is sealed to the locking collar via a compressive spring force seal.

18. The system of claim 17, further comprising a set of instructions; and wherein the system is arranged as a kit.

19. A method for enhanced sealing of coupled medical fluid lines having a threaded connection, the method comprising the steps of:

providing a system for enhanced sealing of coupled medical fluid lines having a threaded connection, the system including a male Luer lock fitting, a female Luer lock fitting, and an annular collar seal, the male Luer lock fitting including a male connector, a locking collar, and a female lock element fixed to the locking collar, the female Luer lock fitting including a female connector, a connector guide extending radially and axially from the female connector, and a male lock element fixed to the connector guide axially opposite the female connector and extending radially outward from the connector guide, and the annular collar seal affixable to locking collar of the male Luer lock fitting and configured to permit passage of the connector guide and the male lock element of the female Luer lock fitting into the locking collar of the male Luer lock fitting, and further configured to seal against the connector guide after said passage of the connector guide and the male lock element;

affixing the annular collar seal to the male Luer lock fitting such that the annular collar seal seals against the locking collar;

fluidly coupling a first medical fluid line to the male connector of the male Luer lock fitting and a second medical fluid line to the female connector of the female Luer lock fitting;

inserting the connector guide and the male lock element of the female Luer lock fitting through the annular collar and onto the male Luer lock fitting;

coupling the male lock element of the female Luer lock fitting with the female lock element of the male Luer lock fitting; and transferring a fluid between the first medical fluid line or vascular access device and the second medical fluid line via the male connector of the male Luer lock fitting and the female connector of the female Luer lock fitting.

20. The method of claim 19, further comprising the step of forming a persistent seal between the annular collar seal and the male Luer lock fitting via at least one of a polymer weld or an adhesive bond.

* * * * *